United States Patent
Pakzaban et al.

(10) Patent No.: US 9,254,160 B2
(45) Date of Patent: Feb. 9, 2016

(54) DRIVER ASSEMBLY WITH GUIDEWIRE CONTROL MECHANISM

(71) Applicant: Aesculap Implant Systems, LLC, Center Valley, PA (US)

(72) Inventors: Peyman Pakzaban, Houston, TX (US); Greg Nelson, Bethlehem, PA (US); Andrew Dauster, Breinigsville, PA (US); Tyler Haskins, Bethlehem, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 386 days.

(21) Appl. No.: 13/826,190

(22) Filed: Mar. 14, 2013

(65) Prior Publication Data

US 2014/0276892 A1 Sep. 18, 2014

(51) Int. Cl.
*A61B 17/88* (2006.01)
(52) U.S. Cl.
CPC .......... *A61B 17/8875* (2013.01); *A61B 17/8894* (2013.01); *A61B 17/8897* (2013.01)
(58) Field of Classification Search
CPC .................. A61B 17/8894; A61B 17/8875
USPC .................. 606/103; 24/115 G, 127, 132 AA
See application file for complete search history.

(56) References Cited

U.S. PATENT DOCUMENTS

| | | | |
|---|---|---|---|
| 6,015,413 A | 1/2000 | Faccioli et al. | |
| 6,719,758 B2 | 4/2004 | Beger et al. | |
| 7,207,995 B1 * | 4/2007 | Vandewalle | 606/104 |
| 7,674,276 B2 * | 3/2010 | Stone et al. | 606/232 |
| 7,842,038 B2 * | 11/2010 | Haddock et al. | 606/79 |
| 8,641,717 B2 * | 2/2014 | Defossez et al. | 606/86 R |
| 2006/0039749 A1 * | 2/2006 | Gawehn | F16B 5/025 403/367 |
| 2010/0139051 A1 * | 6/2010 | Bourke et al. | 24/115 R |

* cited by examiner

*Primary Examiner* — David Bates
(74) *Attorney, Agent, or Firm* — RatnerPrestia

(57) ABSTRACT

An implant driver assembly includes an assembly for advancing a threaded implant over a wire. The assembly may include a driver tool with a proximal end, a distal end and a first engagement surface that has a first thread. The driver tool may also include a first wire passage. The assembly may further include a wire locking mechanism with a second engagement surface having a second thread. The second thread is engaged with the first thread to rotatably couple the wire locking mechanism with the driver tool. The wire locking mechanism may further include a second wire passage. The second wire passage may be substantially coaxially aligned with the first wire passage.

17 Claims, 4 Drawing Sheets

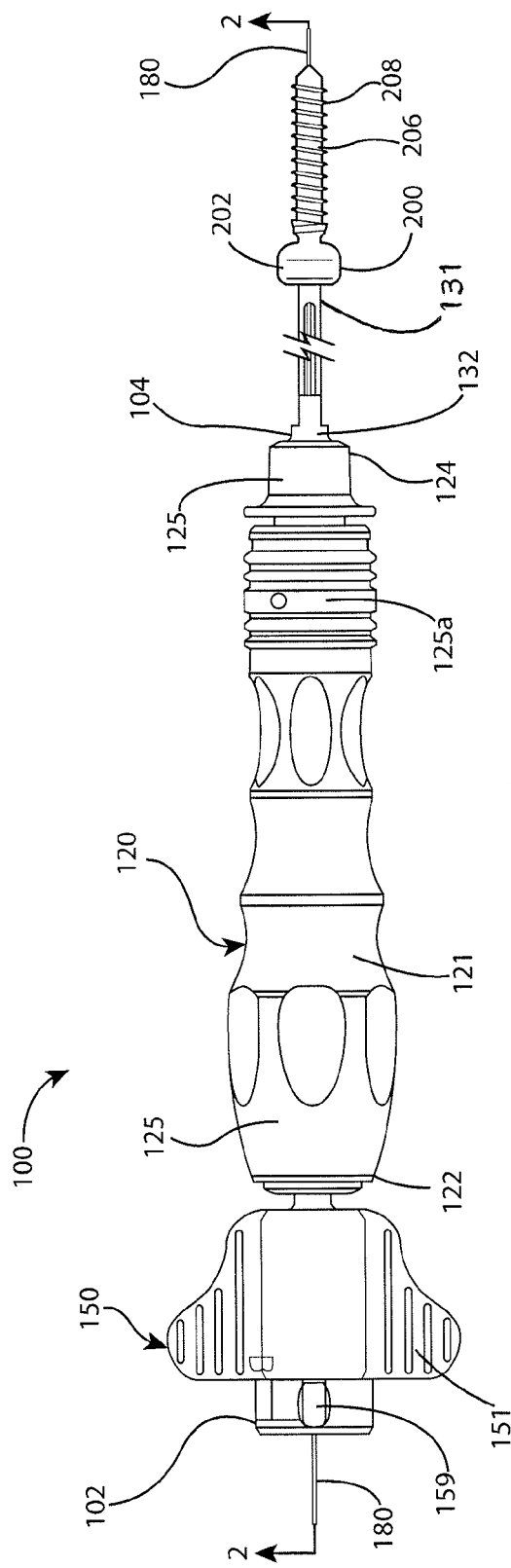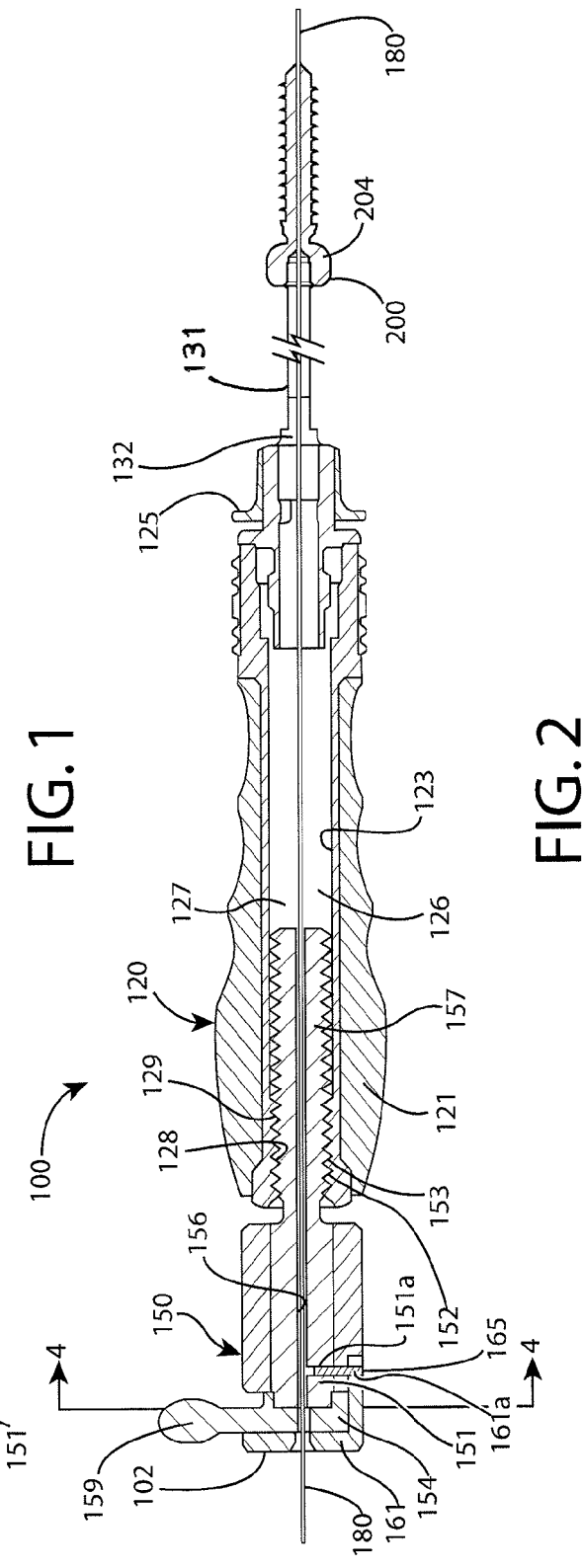

DRIVER ASSEMBLY WITH GUIDEWIRE CONTROL MECHANISM

FIELD

The present disclosure relates generally to instrumentation used with guidewires and the like, and more specifically to instruments used to drive fasteners and other drivable elements over guidewires that guide the trajectory of the elements to a precise location.

BACKGROUND

Surgical procedures that require the insertion of a bone screw often include the use of a wire, such as a "K-wire", to deliver the bone screw to a desired point of insertion. The K-wire is attached to a bone at a desired point of screw insertion, and extends out of the incision. The bone screw is typically cannulated, meaning the screw has a longitudinal passage extending through the screw that allows the screw to be passed over the K-wire. A cannulated driver tool is also passed over the K-wire and engaged with the screw head to drive the screw into the bone at the desired insertion point.

K-wires can create complications as the bone screw is driven over the K-wire. For example, the K-wire can be inadvertently advanced beyond the anterior margin of the bone and damage vital organs as the screw is driven into the bone. In addition, the K-wire can kink during advancement of the screw over the K-wire. These problems can occur if the trajectory of the screw is not precisely aligned with the trajectory of the K-wire.

Surgeons have used two strategies to avoid or mitigate inadvertent advancement of the K-wire. In the first strategy, the surgeon inserts the K-wire only partly into the bone to provide a margin of error that allows for some inadvertent advancement of the K-wire into the bone. This strategy is problematic because there is a risk that the K-wire will be pulled out during the procedure. In the second strategy, the surgeon uses lateral fluoroscopy to monitor the K-wire throughout the screw insertion process. If K-wire advancement is observed under lateral fluoroscopy, the surgeon halts the procedure until steps are done to prevent further advancement. This strategy is also problematic because it exposes the patient to excessive radiation. Neither strategy prevents or addresses the problem of kinking. Therefore, known methods for driving bone screws over K-wires are prone to complications and are in need of improvement.

SUMMARY

Complications experienced with known devices and methods for driving implants over K-wires are avoided or resolved in many respects by implant driver assemblies in accordance with the invention. In one aspect of the invention, an implant driver assembly includes an assembly for advancing a threaded implant over a wire. The assembly includes a driver tool with a proximal end, a distal end and a first engagement surface that has a first thread. The driver tool also includes a first wire passage. The assembly further includes a wire locking mechanism with a second engagement surface having a second thread. The second thread is engaged with the first thread to rotatably couple the wire locking mechanism with the driver tool. The wire locking mechanism further includes a second wire passage. The second wire passage is substantially coaxially aligned with the first wire passage.

In another aspect of the invention, the assembly includes a wire locking mechanism that features a cam device operable to lock a wire relative to the locking mechanism.

In another aspect of the invention, the assembly includes a cam device with a hub portion and a sleeve. The sleeve defines a socket that receives the hub portion. The hub portion defines a first wire conduit, and the sleeve defines a second wire conduit. The first and second wire conduits form adjacent sections of the second wire passage.

In another aspect of the invention, the assembly includes a hub portion and a socket that are cylindrical, and a longitudinal axis of the second wire conduit is radially offset from a longitudinal axis of the socket.

In another aspect of the invention, the assembly includes a sleeve that is axially rotatable relative to the hub portion between a first axial orientation in which a longitudinal axis of the first wire conduit is offset from a longitudinal axis of the second wire conduit by a first distance, and a second axial orientation in which said longitudinal axis of the first wire conduit is offset from said longitudinal axis of the second wire conduit by a second distance, the second distance being greater than the first distance.

In another aspect of the invention, the assembly includes a wire extending through the driver tool and the wire locking mechanism.

In another aspect of the invention, the assembly includes a wire locking mechanism that is moveable between an unlocked position in which the wire is axially displaceable with respect to the wire locking mechanism, and a locked position in which the wire is fixed to the wire locking mechanism.

In another aspect of the invention, the assembly includes a driver tool that is rotatable relative to the wire locking mechanism to advance a cannulated fastener over the wire in a distal direction relative to the locking mechanism.

In another aspect of the invention, the assembly includes a driver tool that is rotatable relative to the wire locking mechanism to advance the cannulated fastener in a distal direction and into a stationary object, and simultaneously draw the wire in a proximal direction and away from the stationary object.

In another aspect of the invention, the assembly includes a driver tool that is rotatable relative to the wire locking mechanism to advance said cannulated fastener in a distal direction and into a stationary object, and simultaneously immobilize the wire with respect to the stationary object.

In another aspect of the invention, the assembly includes a wire locking mechanism that features a shaft, the second engagement surface located on an exterior of the shaft, and the second thread extending along the exterior of the shaft.

In another aspect of the invention, the assembly includes a driver tool that defines a bore with an inner wall, the first engagement surface located on the inner wall, and the first thread extending along the inner wall, the shaft received in the bore.

In another aspect of the invention, the assembly includes a driver tool with a handle. The handle may be located distally relative to the wire locking mechanism, or proximally relative to the wire locking mechanism.

In another aspect of the invention, the assembly includes a driver tool with a distal end defining a driver tip.

In another aspect of the invention, the assembly includes a driver tool with a distal end defining a quick connect socket adapted to receive a driver bit.

In another aspect of the invention, the assembly includes a wire locking mechanism that defines a body portion and a pair of threaded pins threaded into a pair of threaded holes in the body portion. The pins may be diametrically opposed to one another and displaceable toward one another to lock a wire relative to the wire locking mechanism.

In another aspect of the invention, the assembly includes a reverse drive mechanism for driving a wire in a proximal direction relative to the driver tool as the driver tool advances a fastener in a distal direction relative to the wire locking mechanism.

BRIEF DESCRIPTION OF THE DRAWINGS

The foregoing summary and the following description will be better understood in conjunction with the drawing figures, of which:

FIG. 1 is a top view of a driver assembly in accordance with one exemplary embodiment, shown with a fastener;

FIG. 2 is a side cross section view of the driver assembly and fastener in FIG. 1;

DETAILED DESCRIPTION

Figure 3:
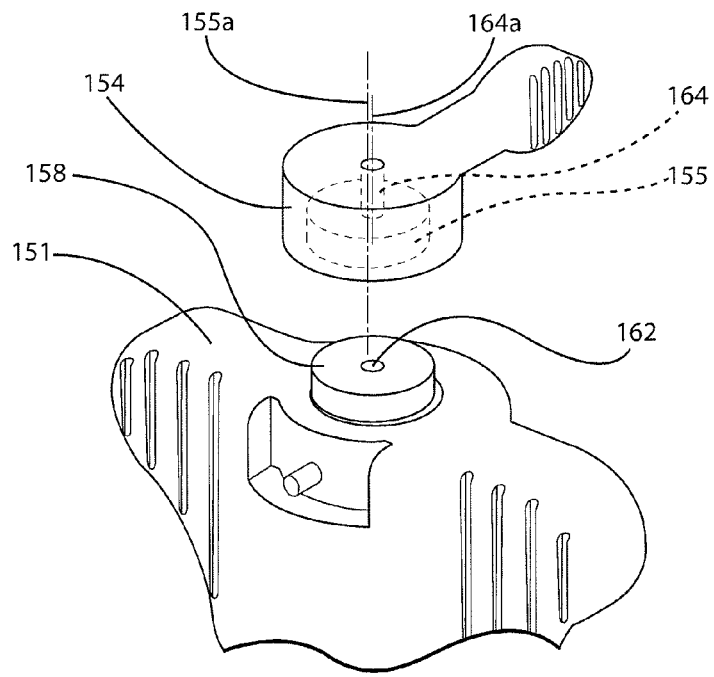
FIG. 3 is an exploded perspective view of components of the driver assembly of FIG. 1, partially truncated, with some components omitted.

Although the invention is illustrated and described herein with reference to specific embodiments, the invention is not intended to be limited to the embodiments and details shown and described. Various modifications may be made in the details within the scope and range of equivalents of the claims and without departing from the invention.

The term "proximal", when used to refer to the relative position of a feature, means a location adjacent to or towards the person holding the device when the device is in use, e.g. a surgeon, mechanic or technician. The term "distal", when used to refer to the relative position of a feature, means a location adjacent to or towards the area on which the device is to be used, or a location remote to the proximal end, e.g. a patient or an item being repaired.

Applicants have developed an instrument in the form of a driver assembly that can be used to advance a drivable element over a wire to an insertion site, while controlling the tension and position of the wire so that the wire does not kink or advance into the insertion site. The driver assembly may include a wire locking mechanism that immobilizes the wire as the driver assembly advances the drivable element over the wire. Alternatively, the driver assembly may include a wire locking mechanism that draws or retracts the wire away from the insertion site. For example, the driver assembly may include a reverse drive mechanism that drives the wire in a proximal direction simultaneously as the driver assembly advances the drivable element in a distal direction.

Driver assemblies in accordance with the invention may be used in any application where an element is advanced over a wire and inserted into an object. Although examples of driver assemblies are primarily described herein in connection with surgical procedures, driver assemblies in accordance with the invention may be used in non-surgical applications as well.

A driver assembly in accordance with one example includes a driver tool and a wire locking mechanism. The driver tool may include a proximal end, a distal end and a first engagement surface with a first thread. The driver tool may further include a first passage for a wire. The wire locking mechanism may include a second engagement surface with a second thread. The second thread may be engaged with the first thread to rotatably couple the wire locking mechanism with the driver tool. The wire locking mechanism may further include a second passage for a wire. The second passage may be coaxially aligned with the first passage.

The wire locking mechanism may include various devices that are operable to lock a wire relative to the locking mechanism. For example, the wire locking mechanism may include a cam device. The cam device may include a hub portion and a sleeve comprising a socket that receives the hub portion. The hub portion may include a first wire conduit, and the sleeve may include a second wire conduit. The first and second wire conduits may form adjacent sections of the second wire passage.

The hub portion and the socket may be cylindrical. The longitudinal axis of the second wire conduit may be radially offset from a longitudinal axis of the socket. The sleeve may be axially rotatable relative to the hub portion between a first axial orientation and a second axial orientation. In the first axial orientation, the longitudinal axis of the first wire conduit is offset from the longitudinal axis of the second wire conduit by a first distance. In the second axial orientation, the longitudinal axis of the first wire conduit is offset from a longitudinal axis of the second wire conduit by a second distance, the second distance being greater than the first distance.

The assembly is intended be used with a wire, including but not limited to a K-wire. The wire may extend through the driver tool and the wire locking mechanism, as part of the overall assembly. The wire locking mechanism may be moveable between an unlocked position and a locked position. In the unlocked position, the wire is axially displaceable with respect to the wire locking mechanism. In the locked position, the wire is fixed to the wire locking mechanism. The driver tool may be rotatable relative to the wire locking mechanism to advance a cannulated implant over the wire in a distal direction relative to the locking mechanism. For example, the driver tool may be rotatable relative to the wire locking mechanism to advance a bone screw in a distal direction and into a stationary object, and simultaneously draw the wire in a proximal direction and away from the stationary object. In addition, or in the alternative, the driver tool may be rotatable relative to the wire locking mechanism to advance a cannulated implant in a distal direction and into a stationary object, and simultaneously immobilize the wire with respect to the stationary object.

The wire locking mechanism may include a shaft, with the second engagement surface located on an exterior of the shaft. The second thread may extend along the exterior of the shaft. The driver tool may include a bore that defines an inner wall, with the first engagement surface located on the inner wall. The first thread may extend along the inner wall, so that the shaft of the wire locking mechanism can be screwed into the bore of the driver tool.

The driver tool may include a handle. The handle of the driver tool may be located distally relative to the wire locking mechanism. Alternatively, the handle of the driver tool may be located proximally relative to the wire locking mechanism. The distal end of the driver tool may include a fixed driver tip integrally formed with the driver tool. Alternatively, the distal end of the driver tool may include a quick connect socket adapted to receive a driver bit.

In other embodiments, the wire locking mechanism may include a body portion and a pair of pins. The pins may be threaded into a pair of threaded holes in the body portion. The pins may be positioned diametrically opposed to one another, and displaceable toward one another to lock a wire relative to the wire locking mechanism. The first thread and the second thread between the driver tool and wire locking mechanism may collectively form a reverse drive mechanism for driving a wire in a proximal direction relative to the driver tool. The reverse drive mechanism may work simultaneously with the driver tool to withdraw the wire in a proximal direction away from an insertion site, at the same moment that the driver tool advances an implant in a distal direction relative to the wire locking mechanism.

Referring now to FIGS. 1 and 2, an implant driver assembly 100 in accordance with one example is shown. Assembly 100 includes a proximal end 102 and a distal end 104. Proximal end 102 is configured to be held and manipulated by a user, such as a surgeon, and distal end 104 is configured to engage and manipulate a bone screw 200. Assembly 100 generally includes a driver tool 120 and a wire locking mechanism 150. Driver tool 120 and wire locking mechanism 150 may be packaged and sold in an assembled state that will be explained in further detail below. In use, the assembly 100 includes a wire in the form of a K-wire 180 that extends through driver tool 120 and locking mechanism 150, and is releasably engaged by the locking mechanism. Driver tool 120 and wire locking mechanism 150 may be packaged, assembled and sold with K-wire 180, or the K-wire may be packaged and sold separately from the driver tool and wire locking mechanism.

Driver tool 120 is preferably a cannulated screw driver, but it is within the scope of the present invention for the driver tool to be any other known or later developed driver tool that is configured to be passed over K-wire 180 when in use. Driver tool 120 includes a body 121 having a proximal end 122, a distal end 124 and a first wire passage 126 extending between the proximal end and distal end, adapted to receive K-wire 180. Proximal end 122 includes a first engagement surface 128 with a first thread 129. First thread 129 extends along an inner wall 123 inside a bore 127 formed inside driver tool 120. Distal end 124 includes a quick-connect type receiver 125 adapted to connect to an extension shaft 131 and a driver bit 132. Driver bit 132 is configured to engage a bone screw 200, the latter having a head 202 with a socket 204 adapted to receive the driver bit, and a shank 206 having an external screw thread 208. Driver bit 132 may include any type of standard tip configuration, including but not limited to flat head, Philips head, hexalobular (Torx®), and other known or later developed configurations capable of engaging bone screw 200. Alternatively, driver tip 132 may be manufactured with a customized configuration. Quick-connect receiver 125 includes an internal gear wheel and two pawls (not shown) that are controlled by a switch 125a that allows driver tool 120 to function as a ratcheting screwdriver in both the clockwise and counterclockwise directions.

Wire locking mechanism 150 includes a second engagement surface 152 in the form of a second thread 153. Second thread 153 extends along the exterior of a shaft 157 that extends from wire locking mechanism 150 and is insertable into the bore 127. Second thread 153 engages with first thread 129 as shown to rotatably couple wire locking mechanism 150 with driver tool 120. Wire locking mechanism 150 includes a second wire passage 156, as described in more detail below. Second wire passage 156 can be aligned with first wire passage 126 to allow driver tool 120 and wire locking mechanism 150 to be passed over K-wire 180.

Wire locking mechanism 150 is moveable between an "unlocked position" and a "locked position" to control relative movement of K-wire 180. When wire locking mechanism 150 is in the unlocked position, K-wire 180 is axially displaceable with respect to the wire locking mechanism. As such, K-wire 180 can be passed through the wire locking mechanism 150 and driver tool 120, and freely slide in a proximal direction or a distal direction with respect to the wire locking mechanism and driver tool. When wire locking mechanism 150 is in the locked position, K-wire is fixed to the wire locking mechanism. This prevents K-wire 180 from advancing in a distal direction as driver tool 120 advances bone screw 200. Fixation of K-wire 180 in the locked position also allows a tension to be applied and maintained on the K-wire to minimize or prevent the K-wire from buckling or kinking as bone screw 200 is advanced.

Driver tool 120 is rotatable relative to wire locking mechanism 150 to advance bone screw 200, or other cannulated implants and fasteners, over K-wire 180 in a distal direction relative to the locking mechanism. In one procedure, driver tool 120 may be rotatable relative to wire locking mechanism 150 to advance bone screw 200 in a distal direction and into a stationary object, and simultaneously draw K-wire 180 in a proximal direction and away from the stationary object. In addition, or in the alternative, driver tool 120 may be rotatable relative to wire locking mechanism 150 to advance bone screw 200 in a distal direction and into the stationary object, and simultaneously immobilize K-wire 180 with respect to the stationary object. The stationary object may be a human or animal bone, an implanted device, or other object.

The relative displacement of K-wire 180 and bone screw 200 are functions of the pitch of first and second threads 129, 153, and the pitch of thread 208 on bone screw 200. K-wire can be drawn in a proximal direction through a distance that is proportional to the distance through which bone screw 200 is advanced in a distal direction. The ratio of K-wire displacement, D1, to screw advancement, D2, depends on the relationship of the pitches of first and second threads 129, 153, and thread 208. For example, the pitch of threads 129, 153 may be identical to the pitch of thread 208 to establish a ratio of D1 to D2 of 1:1. Alternatively, the pitch of threads 129, 153 may be greater than the pitch of thread 208 to establish a higher ratio of D1 to D2, e.g. 2:1. Moreover, the pitch of threads 129, 153 may be less than the pitch of thread 208 to establish a lower ratio of D1 to D2, e.g. 1:2.

Wire locking mechanisms in accordance with the invention may include a variety of mechanisms designed to engage a wire to prevent the wire from kinking or inadvertently advancing into the insertion site. For example, the wire locking mechanism may utilize a clamp, a collet or a wedge-type locking mechanism. Referring to FIGS. 2 and 3, wire locking mechanism 150 includes a wing-shaped handle 151 and a generally cylindrical sleeve 154. Second wire passage 156 passes through handle 151 and sleeve 154 when the handle and sleeve are coupled together. Sleeve 154 is rotatably coupled to handle 151, with the handle and sleeve collectively forming a cam device that operates to lock K-wire 180 relative to locking mechanism 150. A lever 159 extends radially outwardly from sleeve 154 and provides an extension that the user can move to rotate the sleeve.

The cam device includes a hub portion 158 on handle 151 that is configured to extend inside a socket 155 formed in sleeve 154. In the assembled state, socket 155 receives hub portion 158, with sleeve 154 freely rotatable relative to the hub portion. Assembly 100 includes a cylindrical cap 161, which is shown in FIG. 2 but omitted in FIG. 3 for clarity. Cap 161 is secured over sleeve 154 and hub portion 158 when the hub portion is received in the socket. Handle 151 includes a small pin hole 151a that aligns with a pin hole 161a in cap 161. A pin 165 is inserted through the aligned pin holes 151a and 161a to secure cap 161 over sleeve 154 and handle 151.

Hub portion 158 includes a first wire conduit 162, and sleeve 154 includes a second wire conduit 164. First wire conduit 162 and second wire conduit 164 form adjacent sections of second wire passage 156 when sleeve 154 is coupled to handle 151. First wire conduit 162 and second wire conduit 164 are cylindrical and have uniform diameters. Preferably, the first wire conduit 162 has a smaller diameter than the second wire conduit 164.

Sleeve 154, socket 155 and hub portion 158 are all cylindrical. Second wire conduit 164 has a longitudinal axis 164a, and socket 155 has a longitudinal axis 155a that is parallel to longitudinal axis 164a. Socket 155 is not centered with respect to sleeve 154, but rather is off-centered in the sleeve. In contrast, second wire conduit 164 is centered with respect to sleeve 154. Therefore, longitudinal axis 155a of socket 155 is not coaxial with longitudinal axis 164a of second wire conduit 164, as seen in FIG. 3.

Figure 4A:
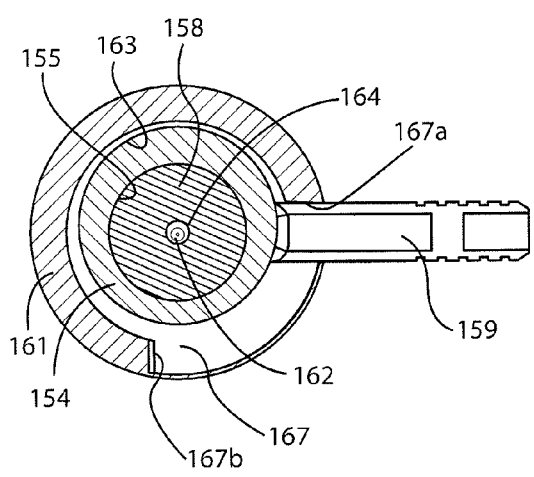
FIG. 4A is a top cross section view of components of a wire locking mechanism in the assembly of FIG. 1, with components shown in a first operative position.
Figure 4B:
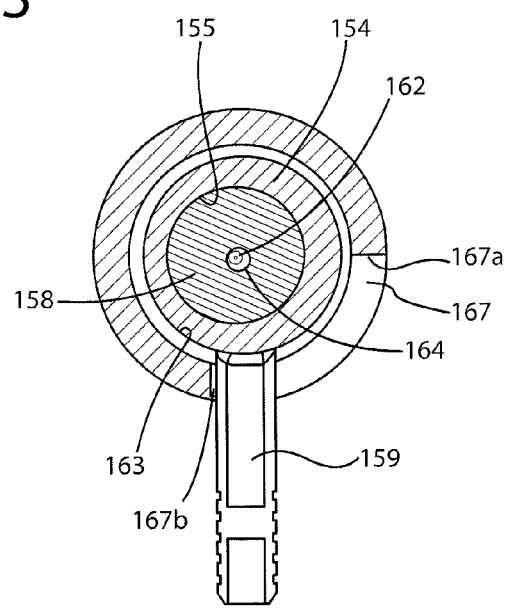
FIG. 4B is a top cross section view of components of a wire locking mechanism in the assembly of FIG. 1, with components shown in a second operative position.

FIGS. 4A and 4B provide cross section views of wire locking mechanism 150 taken through line 4-4 in FIG. 1. The cross section views illustrate wire locking mechanism 150 as it would appear in two operating positions. In the assembled state, sleeve 155 is axially rotatable relative to hub portion 158 and cap 161 between a first axial orientation representing the unlocked position referred to previously, and a second axial orientation representing the locked position referred to previously.

In the first axial orientation (FIG. 4A), longitudinal axis 162a of first wire conduit 162 is offset from longitudinal axis 164a of second wire conduit 164 by a first distance. This first distance is relatively small. In the second axial orientation (FIG. 4B), longitudinal axis 162a of first wire conduit 162 is offset from longitudinal axis 164a of second wire conduit 164 by a second distance. The second distance is greater than the first distance, meaning that second wire conduit 164 becomes less aligned with first wire conduit 162 when sleeve 154 is moved to the second axial orientation. In this arrangement, the clearance provided between first wire conduit 162 and second wire conduit 164 (i.e. the cross-sectional area of the first wire conduit 162 that is aligned in open communication with the second wire conduit 164) decreases as sleeve 154 is rotated from the first axial orientation to the second axial orientation.

The first distance between longitudinal axes 162a and 164a may be as small as a fraction of a millimeter, so that first wire conduit 162 and second wire conduit 164 are substantially aligned with one another. Alternatively, the first distance may be 0 mm, as noted above, in which case first wire conduit 162 and second wire conduit 164 are concentric and aligned coaxially. Hub portion 158 has an edge 163 surrounding first wire conduit 162. When K-wire 180 is inserted through locking mechanism 150, and sleeve 154 is moved toward the second axial orientation, edge 163 impinges or bears against the portion of the K-wire at the point where first wire conduit 162 and second wire conduit 164 meet. In this state, the wire is locked and cannot slide relative to wire locking mechanism 150.

Sleeve 154 can be rotated between the unlocked position and the locked position by rotating the sleeve through a quarter turn (i.e. 90 degrees) relative to hub portion 158. Rotation of sleeve 154 is limited by a slot 167 formed in cap 161. Cap 161 fits over sleeve 154 and lever 159, with the lever projecting through slot 167. Slot 167 is bounded by a first end wall 167a and a second end wall 167b. First end wall 167a abuts lever 159 when sleeve 154 is in the unlocked position, forming a first stop against counterclockwise rotation beyond the unlocked position. Similarly, second end wall 167b abuts lever 159 when sleeve 154 is in the locked position, forming a second stop against clockwise rotation beyond the locked position. The first stop and second stop alert the user when sleeve 154 is in the unlocked position and the locked position, respectively.

Driver tools and wire locking mechanisms can be positioned in different arrangements with respect to one another. Factors that may favor one arrangement over another include, but are not limited to, ergonomics, user preference and the type of application or procedure for which the assembly is used. In FIGS. 1 and 2, driver tool 120 includes a handle 125 that is located distally with respect to handle 151 of wire locking mechanism 150.

Assembly 100 can be used in the following manner. An insertion point on a bone is identified, and an incision is made above the insertion point where bone screw 200 is to be inserted. K-wire 180 is inserted into the bone at the insertion point using known methods. Wire locking mechanism 150 is attached to driver tool 120 by threading shaft 157 into bore 127. Sleeve 154 is then rotated to the first axial orientation to place wire locking mechanism 150 in the unlocked position. Bone screw 200 is attached to the tip of driver tool 120. Bone screw 200, driver tool 120 and wire locking mechanism 150 are then passed over K-wire 180 and advanced toward the bone in accordance with known methods.

When bone screw 200 is ready to be driven into the bone, sleeve 154 is rotated to the second axial orientation, or locked position, to lock K-wire 180 with respect to wire locking mechanism 150. The user then holds wire locking mechanism 150 in one hand, and holds driver tool 120 with the other hand. The user can place either hand on locking mechanism 150 and the other hand on driver tool 120. The hand that is more often used to turn a screw driver will typically be chosen for handle 125 on driver tool 120. Handle 125 of driver tool 120 is rotated clockwise to begin driving bone screw 200 into the bone. As handle 125 rotates clockwise, driver tool 120 and bone screw 200 move in a distal direction to drive the bone screw into the bone. At the same time, the threaded engagement between first thread 129 and second thread 153 acts to push wire locking mechanism 150 in a proximal direction with respect to driver tool 120. In this arrangement, first thread 129 and second thread 153 provide a reverse drive mechanism that withdraws K-wire 180 from the bone as bone screw 200 is driven into the bone. K-wire 180 is thus prevented from being advanced further into the bone with bone screw 200.

Handle 125 on driver tool 120 is located distally with respect to handle 151 of wire locking mechanism 150, as noted above. This allows the user to place their "driving hand", which operates the driver tool, in a distal position with respect to their "stationary hand", which holds the wire locking mechanism. In other embodiments, the relative positions of the handles are reversed, so that the handle of the driver tool is located proximal to the handle of the wire locking mechanism.

Figure 5:
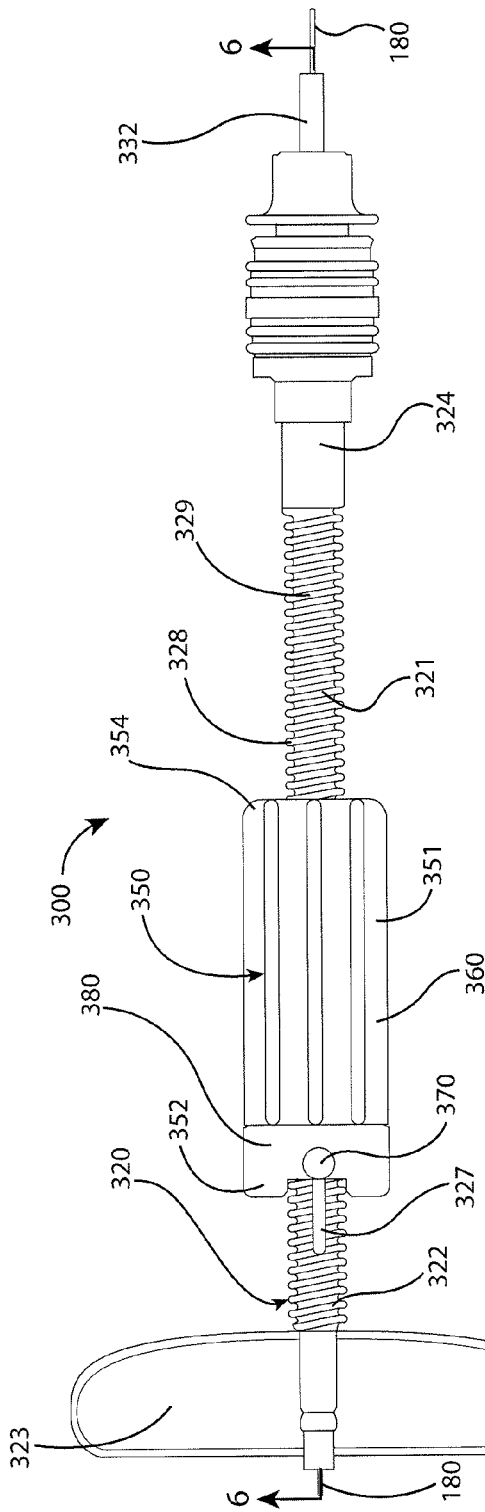
FIG. 5 is a top view of a driver assembly in accordance with another exemplary embodiment.
Figure 6:
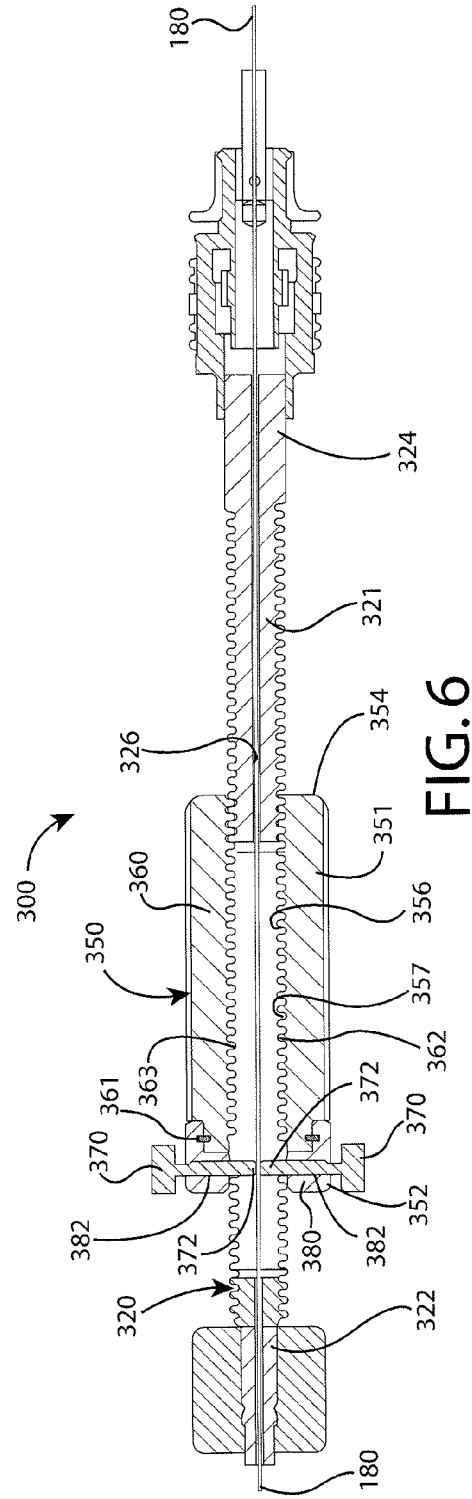
FIG. 6 is a side cross section view of the driver assembly in FIG. 5.

One example of a reversed arrangement is shown in FIGS. 5 and 6, which shows an assembly 300 in accordance with another exemplary embodiment. Assembly 300 includes a driver tool 320 and a wire locking mechanism 350 coupled to a midsection of the driver tool. Driver tool 320 has an elongated shaft 321 that includes a proximal end 322, a distal end 324 and a wire passage 326 extending between the proximal end and distal end. Proximal end 322 includes a T-handle 323. Shaft 321 includes a first engagement surface 328 in the form of a first thread 329 that extends along a substantial portion of the length of the body. Distal end 324 includes a driver tip 332 configured to engage a bone screw, similar to driver tip 132 of driver tool 120.

Wire locking mechanism 350 includes a generally cylindrical body 351 that circumscribes the shaft 321 of driver tool. Body 351 has a proximal end 352, a distal end 354 and an internal bore 356 extending between the proximal and distal ends. Bore 356 is surrounded by an inner wall 357. A second engagement surface 362 in the form of a second thread 363 extends along inner wall 357. Driver tool 320 extends through bore 356, with second thread 363 engaged with first thread 329 as shown to rotatably couple wire locking mechanism 350 with the driver tool. In this assembled arrangement, driver tool 320 and wire locking mechanism 350 can be passed over a K-wire 180.

Assembly 300 provides an alternate configuration that allows the user's driving hand to be placed proximal to the user's stationary hand. This arrangement may be more preferable to users who wish to apply rotational force to the proximal-most end of the assembly, as opposed to a midsection of the assembly.

Body 351 includes a base 360 and a cap 380 rotatably coupled to the base by a bearing 361 as shown in FIG. 6. A pair of threaded pins 370 are threaded into a pair of threaded holes 382 in cap 380. Pins 370 are diametrically opposed to one another in cap 380. Each pin 370 has a distal clamping end 372. The pins 370 can be advanced through cap 380 and toward one another until clamping ends 372 engage K-wire 180. Clamping ends 372 apply radial pressure on K-wire 180 to fix the position of the K-wire so the K-wire cannot move relative to wire locking mechanism 350. Shaft 321 of driver tool 320 includes a pair of diametrically opposed slots 327 that receive the diametrically opposed pins 370 in a captive condition. When T-handle 323 and shaft 321 are rotated to drive a bone screw, pins 370 and cap 380 rotate in unison with the shaft because the pins are captive in slots 327. At the same time, base 360 travels along shaft 321 due to the threaded engagement between first thread 329 and second thread 363. Wire locking mechanism 350 therefore travels along the length of shaft 321 when T-handle 323 is rotated relative to base 360. Cap 380 rotates relative to base 360, and the pins 370 travel axially in slots 327.

When T-handle 323 is rotated in a clockwise direction to drive a bone screw into bone, wire locking mechanism 350 travels towards proximal end 322 of driver tool 320, and away from the bone screw insertion point. When pins 370 are in the locked condition to fix the K-wire, the K-wire is reverse-driven and withdrawn away from the screw insertion point.

Figure 7:
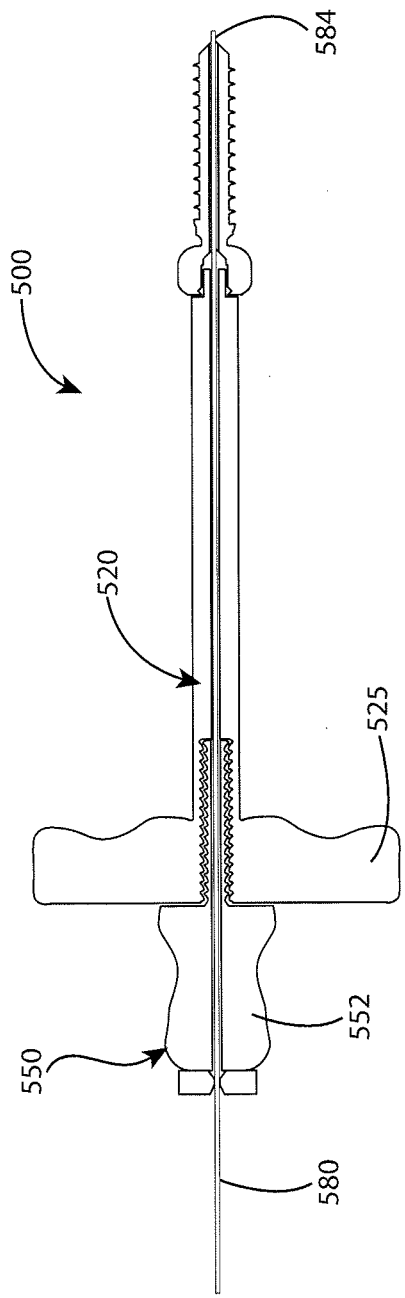
FIG. 7 is a side cross section view of a driver assembly in accordance with another exemplary embodiment, with components shown in a first operative position.
Figure 8:
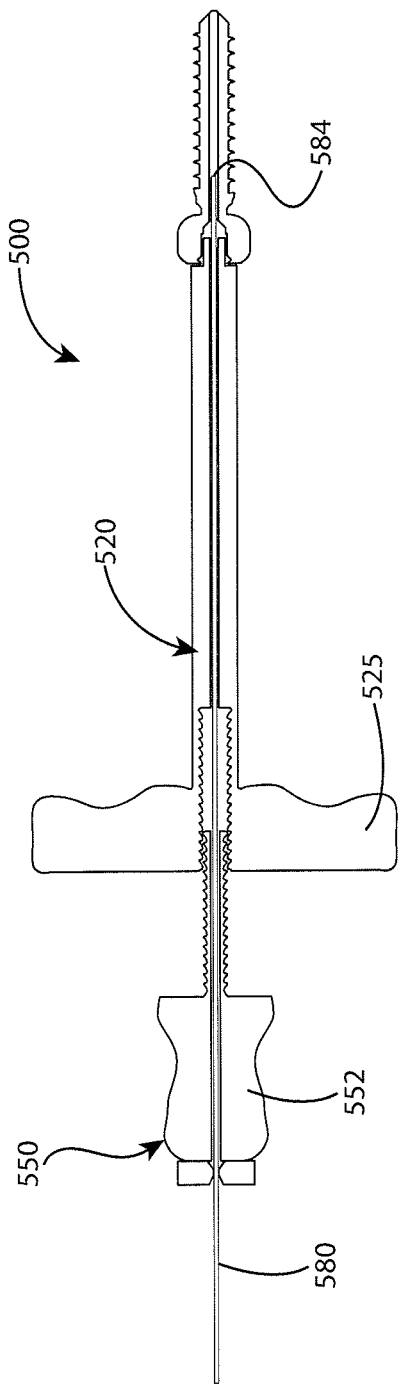
FIG. 8 is a side cross section view of the driver assembly in FIG. 7, with components shown in a second operative position.

Driver tools and wire locking mechanisms may include any type and combination of handle configurations, the selection of which may depend on factors including but not limited to ergonomics, user preference, and the type of application or procedure for which the assembly is used. Referring to FIGS. 7 and 8, another assembly 500 is shown. Assembly 500 is similar to assembly 100 in many respects, but includes a wire locking mechanism 550 with an hour-glass shaped handle 552, and a driver tool 520 with a T-shaped handle 525. Assembly 500 also includes a K-wire 580, similar to K-wire 180. FIG. 7 schematically shows assembly 500 before a screw 600 is driven over wire 580, with a distal end 584 of the wire projecting past the distal end of the screw. FIG. 8 schematically shows assembly 500 after the screw 600 is driven over wire 580, with distal end 584 of wire 580 withdrawn into the screw as a result of wire locking mechanism 550 being displaced in the proximal direction relative to driver tool 520.

Driver tools and wire stopping mechanisms may also include a variety of drive mechanisms. Although drive mechanisms have been shown in the form of threaded surfaces, drive mechanisms may also include gear wheels and clutches that move the gear wheels into engagement with the K-wire. The K-wire itself may include a thread, a series of teeth, or other engagement surfaces that cooperatively engage the gear wheels.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. An implant driver assembly for advancing a threaded implant over a wire, the assembly comprising:
    a driver tool comprising a proximal end, a distal end and a first engagement surface comprising a first thread, the driver tool further comprising a first wire passage; and
    a wire locking mechanism comprising a second engagement surface comprising a second thread, the second thread engaged with the first thread to rotatably couple the wire locking mechanism with the driver tool, the wire locking mechanism further comprising a second wire passage, the second wire passage substantially coaxially aligned with the first wire passage,
    the wire locking mechanism comprising a cam device operable to lock a wire relative to the locking mechanism,
    the cam device comprising a hub portion and a sleeve, the sleeve comprising a socket that receives the hub portion, the hub portion comprising a first wire conduit and the sleeve comprising a second wire conduit, the first and second wire conduits forming adjacent sections of the second wire passage,
    the hub portion defining a maximum diameter section and the socket defining a socket diameter, the socket diameter greater than the diameter of the maximum diameter section of the hub portion and sized to receive the maximum diameter section of the hub portion.

2. The assembly of claim 1, wherein the hub portion and the socket are cylindrical, wherein a longitudinal axis of the second wire conduit is radially offset from a longitudinal axis of the socket.

3. The assembly of claim 2, wherein the sleeve is axially rotatable relative to the hub portion between a first axial orientation in which a longitudinal axis of the first wire conduit is offset from a longitudinal axis of the second wire conduit by a first distance, and a second axial orientation in which said longitudinal axis of the first wire conduit is offset from said longitudinal axis of the second wire conduit by a second distance, the second distance being greater than the first distance.

4. The assembly of claim 1, further comprising a wire extending through the driver tool and the wire locking mechanism.

5. The assembly of claim 4, wherein the wire locking mechanism is moveable between an unlocked position in which the wire is axially displaceable with respect to the wire locking mechanism, and a locked position in which the wire is fixed to the wire locking mechanism.

6. The assembly of claim 4, wherein the driver tool is rotatable relative to the wire locking mechanism to advance a cannulated fastener over the wire in a distal direction relative to the locking mechanism.

7. The assembly of claim 6, wherein the driver tool is rotatable relative to the wire locking mechanism to advance said cannulated fastener in a distal direction and into a stationary object, and simultaneously draw the wire in a proximal direction and away from the stationary object.

8. The assembly of claim 6, wherein the driver tool is rotatable relative to the wire locking mechanism to advance said cannulated fastener in a distal direction and into a stationary object, and simultaneously immobilize the wire with respect to the stationary object.

9. The assembly of claim 1, wherein the wire locking mechanism comprises a shaft, the second engagement surface located on an exterior of the shaft, and the second thread extending along said exterior of the shaft.

10. The assembly of claim 9 , wherein the driver tool comprises a bore that defines an inner wall, the first engagement surface located on the inner wall, and the first thread extending along the inner wall, the shaft received in the bore.

11. The assembly of claim 1, wherein the driver tool comprises a handle.

12. The assembly of claim 11, wherein the handle of the driver tool is located distally relative to the wire locking mechanism.

13. The assembly of claim 11, wherein the handle of the driver tool is located proximally relative to the wire locking mechanism.

14. The assembly of claim 1, wherein the distal end of the driver tool comprises a driver tip.

15. The assembly of claim 1, wherein the distal end of the driver tool comprises a quick connect socket adapted to receive a driver bit.

16. The assembly of claim 1, wherein the wire locking mechanism comprises a body portion and a pair of threaded pins threaded into a pair of threaded holes in the body portion, the pins diametrically opposed to one another and displaceable toward one another to lock a wire relative to the wire locking mechanism.

17. The assembly of claim 1, wherein the first thread and the second thread comprise a reverse drive mechanism for driving a wire in a proximal direction relative to the driver tool as the driver tool advances a fastener in a distal direction relative to the wire locking mechanism.

* * * * *